United States Patent [19]
Stoop

[11] Patent Number: 5,792,193
[45] Date of Patent: Aug. 11, 1998

[54] PACEMAKER SYSTEM AND METHOD WITH VENTRICULAR RATE SMOOTHING DURING HIGH RATE ATRIAL ARRHYTHMIA

[75] Inventor: Gustaaf A. P. Stoop, Dieren, Netherlands

[73] Assignee: Vitatron Medical, B.V., Dieren, Netherlands

[21] Appl. No.: 744,060

[22] Filed: Nov. 5, 1996

[51] Int. Cl.$^6$ ............................................. A61N 1/368
[52] U.S. Cl. ............................................. 607/14
[58] Field of Search ............................................. 607/14, 9

[56] References Cited

U.S. PATENT DOCUMENTS

| | | | |
|---|---|---|---|
| 4,945,909 | 8/1990 | Fearnot et al. | 607/14 |
| 5,374,280 | 12/1994 | Den Dulk | 607/14 |
| 5,480,413 | 1/1996 | Greenhut et al. | 607/14 |
| 5,540,726 | 7/1996 | Bonnet et al. | 607/14 |
| 5,545,185 | 8/1996 | Denker | 607/14 |
| 5,591,215 | 1/1997 | Greenhut et al. | 607/14 |

OTHER PUBLICATIONS

Wittkampf, F.H.M. et al., "Rate Stabilization by Right Ventricular Pacing in Patients With Atrial Fibrillation," PACE, vol. 9, Nov.–Dec. 1986, Part II, pp. 1147–1153.
Wittkampf, F.H.M. et al., "Effect of Right Ventricular Pacing on Ventricular Rhythm During Atrial Fibrillation," JACC vol. II, No. 3, Mar. 1988: pp. 539–545.
Chu–Pak Lau, et al., "A New Pacing Method for Rapid Regularization and Rate Control in Atrial Fibrillation," The American Journal of Cariology, vol. 65, May 15, 1990, pp. 1198–1203.

*Primary Examiner*—Marvin M. Lateef
*Assistant Examiner*—Kennedy J. Schaetzle
*Attorney, Agent, or Firm*—Woodcock Washburn Kurtz Mackiewicz & Norris LLP

[57] ABSTRACT

A dual chamber pacemaker and method for ventricular rate smoothing during high rate episodes such as atrial fibrillation are provided. The pacemaker determines when there is a pathologically high atrial rate episode, such as by determining when atrial senses correspond to a spontaneous atrial rate above a predetermined upper rate limit. When such an episode is determined, the pacemaker determines a ventricular pacing escape interval, corresponding to a flywheel rate, the flywheel rate being set at the beginning of the episode to substantially equal the atrial rate just before the high rate episode. As long as the episode continues, the flywheel rate is incremented upward whenever a ventricular sense occurs, thereby following the average ventricular rate; whenever the flywheel escape interval times out and a ventricular pace is delivered, the flywheel rate is decremented. By allowing ventricular senses and pacing only after timeout of an escape interval which substantially equals average ventricular rate, the episode is treated by smoothing out ventricular rate variations while substantially maintaining the ventricular rate that would otherwise occur.

13 Claims, 4 Drawing Sheets

PACEMAKER SYSTEM AND METHOD WITH VENTRICULAR RATE SMOOTHING DURING HIGH RATE ATRIAL ARRHYTHMIA

FIELD OF THE INVENTION

This invention relates to dual chamber pacemaker systems and, more particularly, dual chamber pacemakers which detect high rate atrial arrhythmias such as atrial fibrillation and respond with a specific mode of ventricular pacing during such periods of atrial arrhythmias.

BACKGROUND OF THE INVENTION

Dual chamber pacemakers provide the capacity to optimize cardiac function by coordinating delivery of a ventricular pace pulse (VP) with the preceding atrial event, i.e., a sensed atrial signal (AS) or a delivered atrial pace pulse (AP). Thus, in a VDD(R) or DDD(R) pacemaker system, the underlying sinus rhythm can be tracked as long as it is normal and physiological, with VPs being delivered after time out of an AV delay following the preceding atrial event. However, sensed atrial signals may not always be tracked, and the pacemaker must be able to recognize this condition when it occurs, and deal with it. A significant problem area for pacemaker patients, as well as pacemaker designers, has been that of dealing with high rate atrial arrhythmias. For some patients, during episodes of atrial fibrillation some of the atrial signals are conducted through to the ventricle, but in a random manner which results in large ventricular rate variations which can be difficult for the patient to tolerate. In such situations, the need is to provide ventricular rate stabilization in a way that achieves long term improvement in cardiac performance and clinical symptoms. This problem has been approached historically by providing for the pacemaker to respond by aggressively taking over and pacing at a higher, but safe and more stable rate. See, for example, U.S. Pat. No. 5,480,413, where when a pathologically high atrial rate is detected, the pacemaker paces the ventricle asynchronously and steps up pacing rate until the ventricular rate is substantially stable, or a high rate limit has been reached. A similar approach is disclosed in "Rate Stabilization by Right Ventricular Pacing in Patients with Atrial Fibrillation", PACE, vol 9, pp 1147-53, Nov-Dec, 1986, and "Effect of Right Ventricular Pacing on Ventricular Rhythm during Atrial Fibrillation", JACC Vol 11, pp 539–45, Mar., 1988, Wittkampf and De Jongste. In these disclosures, the aim is continuous overdrive of spontaneous R-wave activity, which is done by adjusting pacing escape interval so that very few R-waves occur spontaneously before the ventricle is paced, but with the result of an even higher average ventricular rate. See also "A New Pacing Method for Rapid Regularization and Rate Control in Atrial Fibrillation", Am Journal of Cardiology, Vol 65, pp 1198–1203, May 15, 1990, Lau et al., which describes an attempt to stabilize by delivering a VP somewhat mid-cycle after a VS, but doesn't effectively smooth out the ventricular rate. While the first objective is rate smoothing in order to minimize the effect of the relatively wild ventricular rate swings, it is also important to smooth out the rates swings without significantly increasing the average rate.

SUMMARY OF THE INVENTION

It is an object of the invention to provide a dual chamber pacemaker with an improved response to high rate atrial arrhythmias such as atrial fibrillation, and in particular to control ventricular rate variations during such arrhythmia episodes.

In accord with the above object, there is provided an algorithm for use with a dual chamber pacemaker during an episode of atrial fibrillation or the like, which algorithm provides for determination of the average ventricular rate and using this to set the ventricular pacing rate, or flywheel rate. Spontaneous R waves can occur before time out of the escape interval corresponding to the flywheel rate, but whenever the escape interval times out a VP is delivered. By this algorithm, average ventricular rate remains about the same as would otherwise be the case, but the wide ventricular rate variations which would otherwise occur are substantially removed.

DESCRIPTION OF THE PREFERRED EMBODIMENTS

Figure 1:
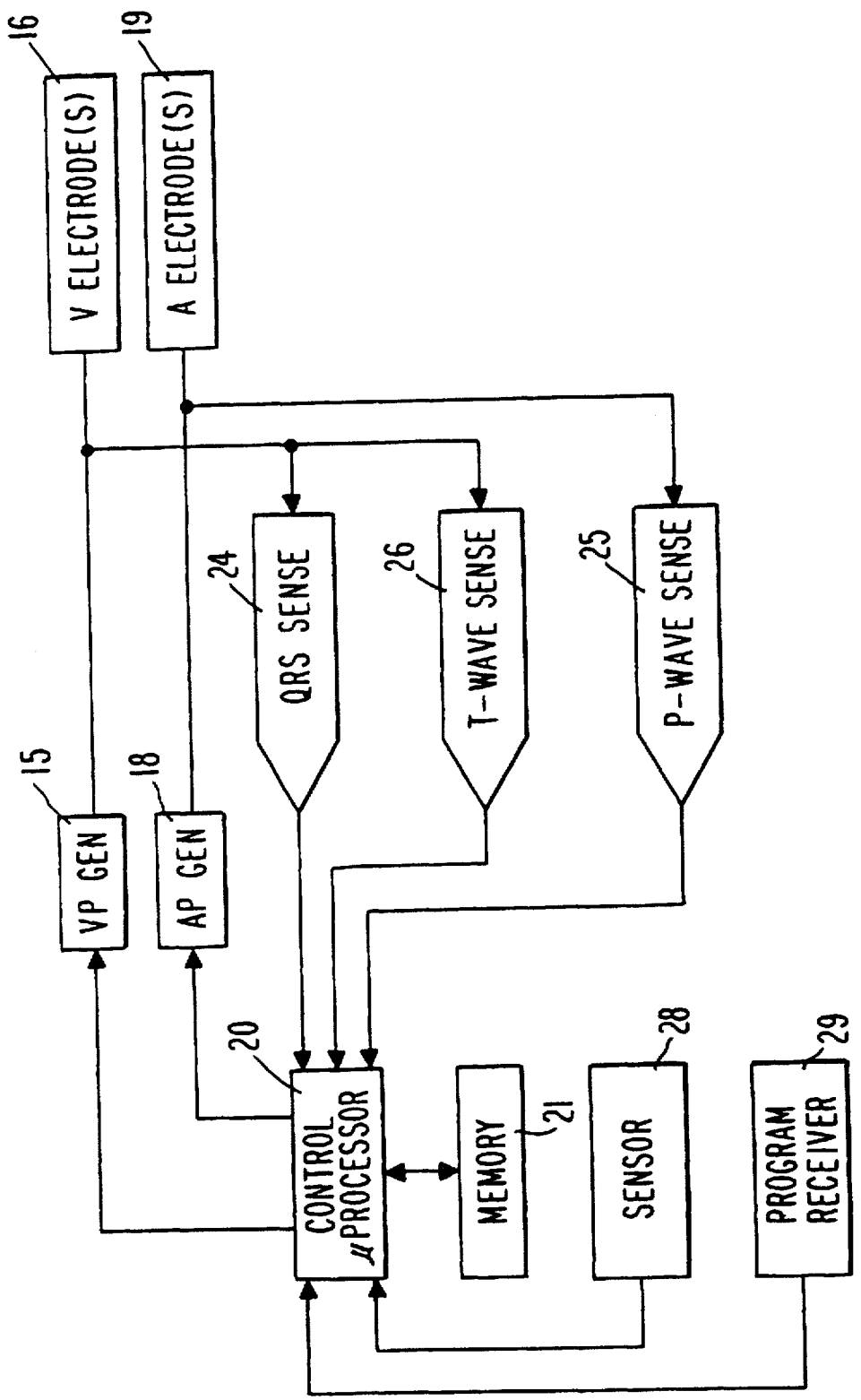
FIG. 1 is a block diagram showing the primary components of a pacemaker in accordance with this invention.

Referring now to FIG. 1, there is shown a pacemaker system having a ventricular pace generator 15 which provides ventricular pace pulses which are delivered across ventricular electrodes 16 to the patient's ventricle. Similarly, an atrial pulse generator 18 is provided for generating atrial pace pulses which are delivered across atrial electrodes 19, to the patient's atrium. Of course, it is to be understood that the pacemaker system may employ either unipolar or bipolar leads. Signals sensed at the ventricular electrodes 16 are connected to a QRS sense amplifier circuit 24, which provides outputs to control circuit 20 to indicate the occurrence of a natural QRS, or VS. Likewise, atrial contractions, or P-waves sensed at atrial electrodes 19 are connected through P-wave sense amplifier circuitry 25, the output of which is connected to control circuit 20. Control circuit 20 suitably contains a microprocessor and associated memory 21, for carrying out normal timing and control functions. Additionally, the control processor is utilized for carrying out, preferably under software control, the rate smoothing routine of this invention, as described in detail in FIG. 5.

Still referring to FIG. 1, a sensor 28 is shown for detecting parameter signals for use in rate responsive control, as is well known in the art. Sensor 28 may be an activity sensor, or sense any other variable which is known to correlate with desired pacing rate, and indeed may comprise two or more such sensors. In another preferred embodiment, QT is used as the rate responsive variable, in which case a T-wave sense amplifier and associated circuitry is utilized as shown in 26, providing an output which is coupled to the control circuitry 20. Also shown is a program receiver 29, for receiving signals from an external programmer, which received signals are delivered to control block and/or to memory 21.

Figure 2:
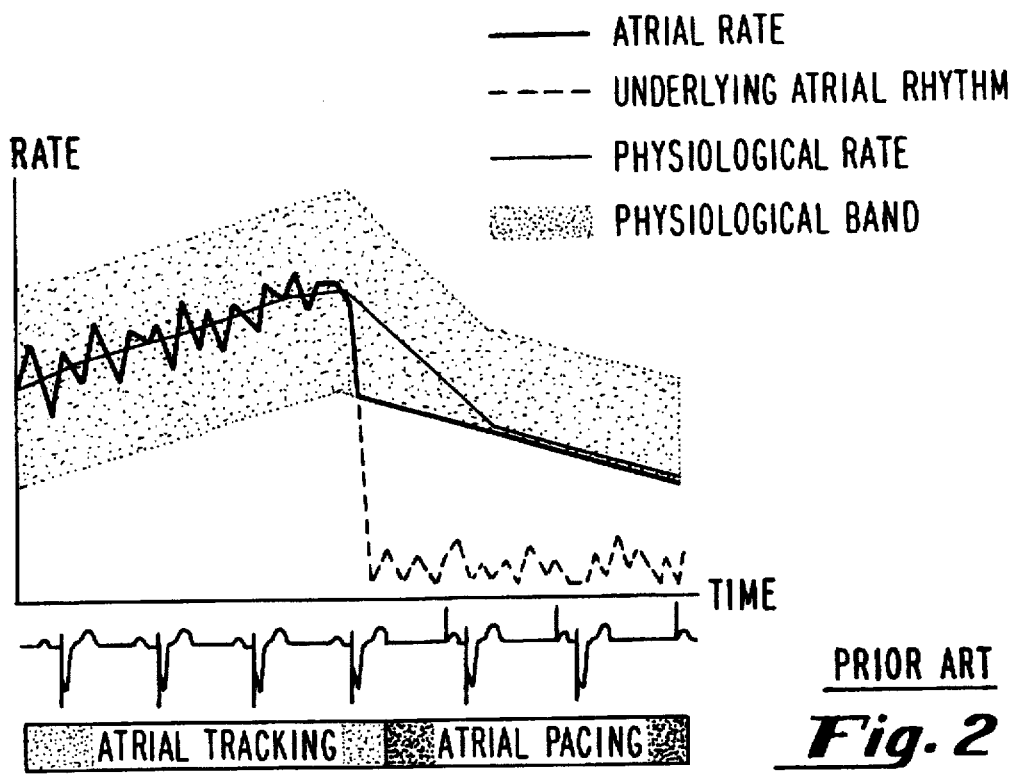
FIG. 2 is a diagram showing decision rates and the concept of a physiological band as found in a prior art pacemaker.

Referring now to FIG. 2, there is shown a diagram illustrating the use of the decision rates for determining when atrial signals are and are not tracked in a dual chamber pacemaker. Reference is made to U.S. Pat. No. 5,247,930, which describes such decision rates in detail, which patent is incorporated herein by reference. In this arrangement, the pacemaker interprets each atrial event as either physiological or pathological, tracking the physiological atrial events but not the pathological atrial events. Thus, atrial senses which occur at too high a rate, or represent too abrupt an increase in rate compared to past atrial signals, are determined to be pathological, and are not tracked. In the case of brady arrhythmia, the pacemaker paces the atrium, or the ventricle in DDD(R) or VDD(R) modes, at the sensor indicated rate.

In order to distinguish between such physiological and pathological atrial events, the pacemaker uses a "physiological rate" and a "physiological band." By definition, the physiological rate is a moving average of the rate that determines the ventricular rate. In case of an underlying sinus rhythm, as for a VDD pacemaker, physiological rate (phys_rate) is determined by sensed atrial events, i.e., it essentially tracks the atrial rate. If the RR sensor determines the ventricular rate, then the physiological rate is based on the sensor rate. In ventricular pacing modes, the physiological rate is based on the spontaneous ventricular rate or the sensor rate. The $phys_{13}$ is updated each pacemaker cycle, the change being generally limited to a predetermined amount, e.g., two BPM per beat. This allows the physiological rate to follow physiological changes of the sinus rate, but prevents it from following abrupt changes. The phys_rate also is limited between the programmed lower rate limit and the maximum sensor or tracking rate, whichever is highest.

Referring to FIG. 2, there is shown a physiological band which is positioned symmetrically around the phys_rate. This band defines rates within which sensed atrial signals can be tracked, i.e., if an AS occurs at an interval corresponding to a rate with in the band, the pacemaker can track it, but not otherwise. The band is coupled to the phys_rate and, for example, may extend to 15 bpm above and below and the phys_rate. Thus, the upper boundary or dynamic tracking limit of the phys_band is equal to the phys_rate+ 15 bpm if the pacemaker is set for automatic mode switching. The lower boundary of the physiological band is equal to the phys_rate−15 bpm if "flywheel" is on, such that the flywheel rate (or dynamic pacing limit) is coupled to $phys_{13}$ as long as physiological atrial signals are sensed. If the sensor rate is higher than the flywheel rate, causing atrial pacing, then $phys_{13}$ is set equal to the sensor rate. The flywheel rate is thus an escape rate defined as the physiological rate−15 bpm, and defines the lower boundary of the physiological band. The flywheel rate cannot exceed the maximum sensor rate or the maximum tracking rate, minus 15 bpm, whichever is lower. The flywheel rate being a dynamic lower pacing rate, is intended to prevent sudden rate decreases upon occurrence of bradyarrhythmia. Thus, during brady conditions when the flywheel escape interval is timed out, the pacemaker paces at the flywheel rate. The flywheel rate is then slowly decreased, e.g., by 2 bpm or 0.5 bpm, continuing until either (1) the lower rate limit is reached; (2) the sensor rate is reached; or (3) the spontaneous rate exceeds the flywheel rate.

Figure 3:
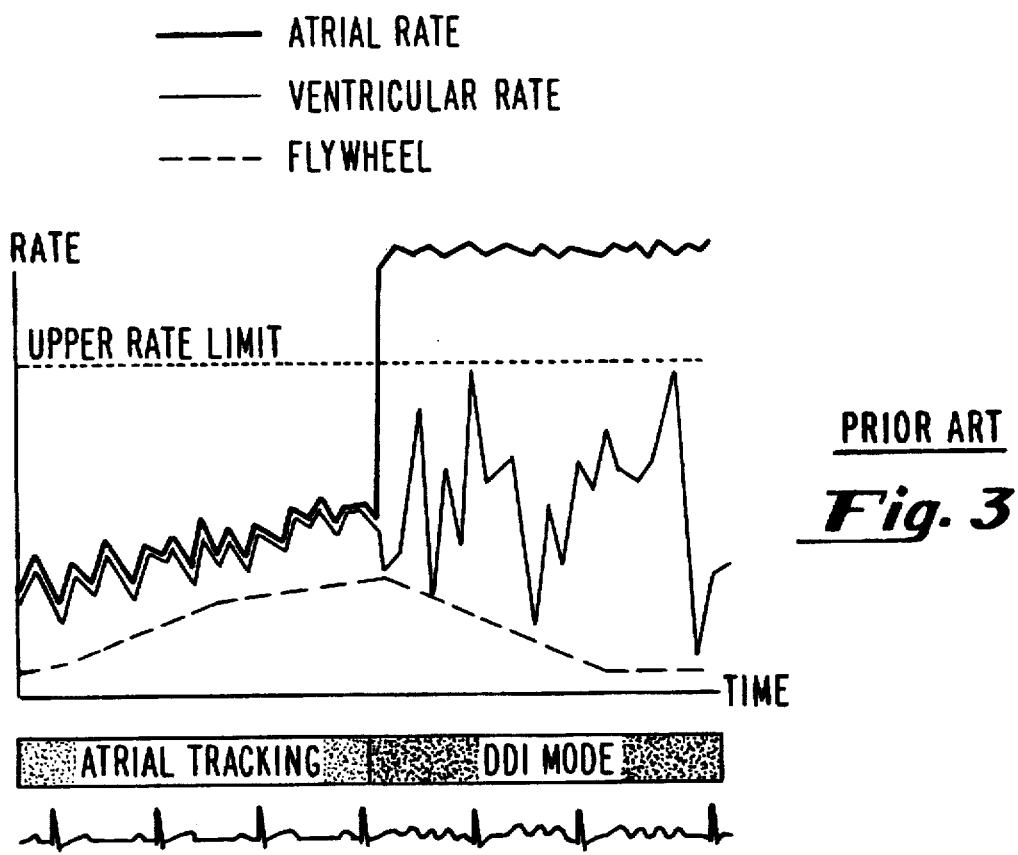
FIG. 3 is a diagram showing the reaction of the prior art pacemaker of FIG. 2 to a high atrial rate, illustrating large ventricular rate variations.

This invention is directed to treating the particular situation of paroxysmal atrial tachycardias where the patient has some degree of AV conduction. In these circumstances, the physiological rate of the described pacemaker (and therefore the ventricular escape rate), would move down to the lower rate limit or the sensor rate, as illustrated in FIG. 3. Under these circumstances, and considering that some of the atrial signals will be conducted through to the ventricle, there is a resulting condition of large spontaneous ventricular interval variations. Thus, in the presence of pathologically high atrial signals, there is some conduction through to the ventricle resulting in some spontaneous ventricular beats which occur at random intervals, such that there are great changes in V—V interval. Any VS between the flywheel rate and the upper rate limit resets the pacemaker timing. Due to the lowered flywheel rate, and the random nature of the conducted beats, the patient endures great variations in ventricular rate, causing substantial discomfort.

Figure 4A:
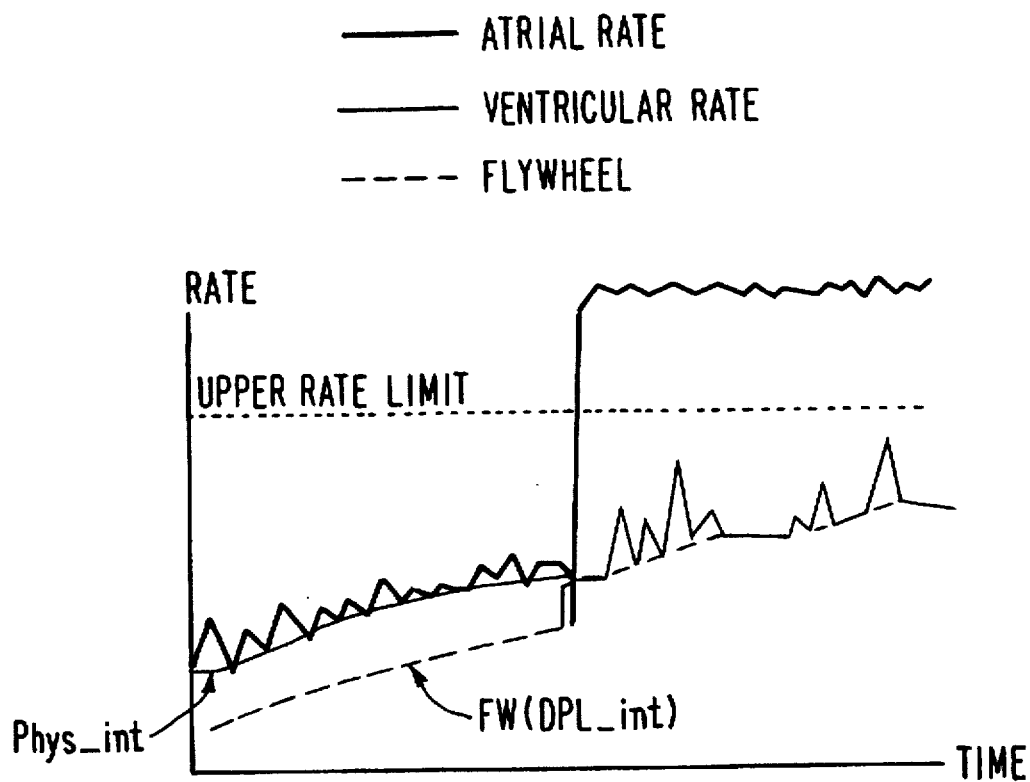
FIG. 4A is a diagram illustrating how flywheel rate, or ventricular pacing rate, follows a high atrial rate in the pacemaker of this invention.
Figure 4B:
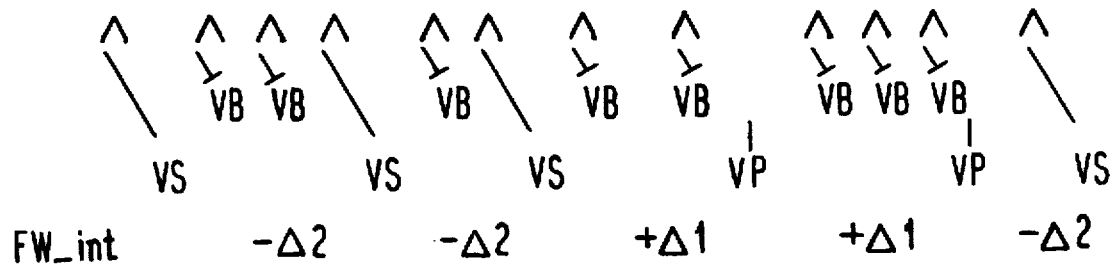
FIG. 4B is a diagram, further illustrating how flywheel is varied to provide ventricular rate smoothing.

The pacemaker of this invention provides a rate smoothing effect which is illustrated in FIG. 4A, where the same atrial signal is presumed as represented in FIG. 3. As seen, prior to the high atrial rate episode, the flywheel (FW) tracks below phys_rate. When the physiologically high atrial rate is sensed, the flywheel rate is immediately adapted to phys_rate, and thereafter phys_rate follows the average ventricular rate. The flywheel rate may be allowed to drop below the average ventricular or phys_rate, e.g., about 2.5 bpm below the average phys_rate. When a ventricular sense occurs corresponding to a rate above phys_rate, phys_rate and FW are incremented upwardly so as to follow the average ventricular rate. However, whenever a VP is delivered upon timeout of the FW escape interval, flywheel is decelerated, or decremented by a programmable step of 2 bpm per minute (fast), 1 bpm per minute (medium fast), or by slower steps. Thus, natural VSs are not overdriven, but allowed to occur, which maintains ventricular rate average close to where it would have otherwise been; but by raising the flywheel pacing rate to this average, or just below such average, random longer intervals are avoided. Due to the nature of the AV conduction system, the very short intervals become suppressed. The result is that average rate is little changed, but variations are substantially minimized in both ways.

Further illustrating the basic aspects of this rate smoothing technique, reference is made to the timing diagram of 4B. The upper line illustrates pathologically high rate atrial senses. As indicated, some but not all of these result in conduction and a resulting VS. Some of the atrial beats are not conducted, and are shown as VB. Due to the random nature of the conduction, the interval from one VS to the next varies, which would otherwise result in the wide ventricular rate swings discussed above. When the FW_times out, a VP is delivered, and the flywheel interval is incremented by Δ1 (corresponding to a decreased flywheel rate). At each occurrence of a VS, corresponding to a higher rate, the flywheel interval is decremented by a predetermined amount Δ2, corresponding to an increased flywheel rate. The respective up and down variations in flywheel rate maintain it at a relatively constant average value, achieving rate smoothing without too high a rate.

Figure 5:
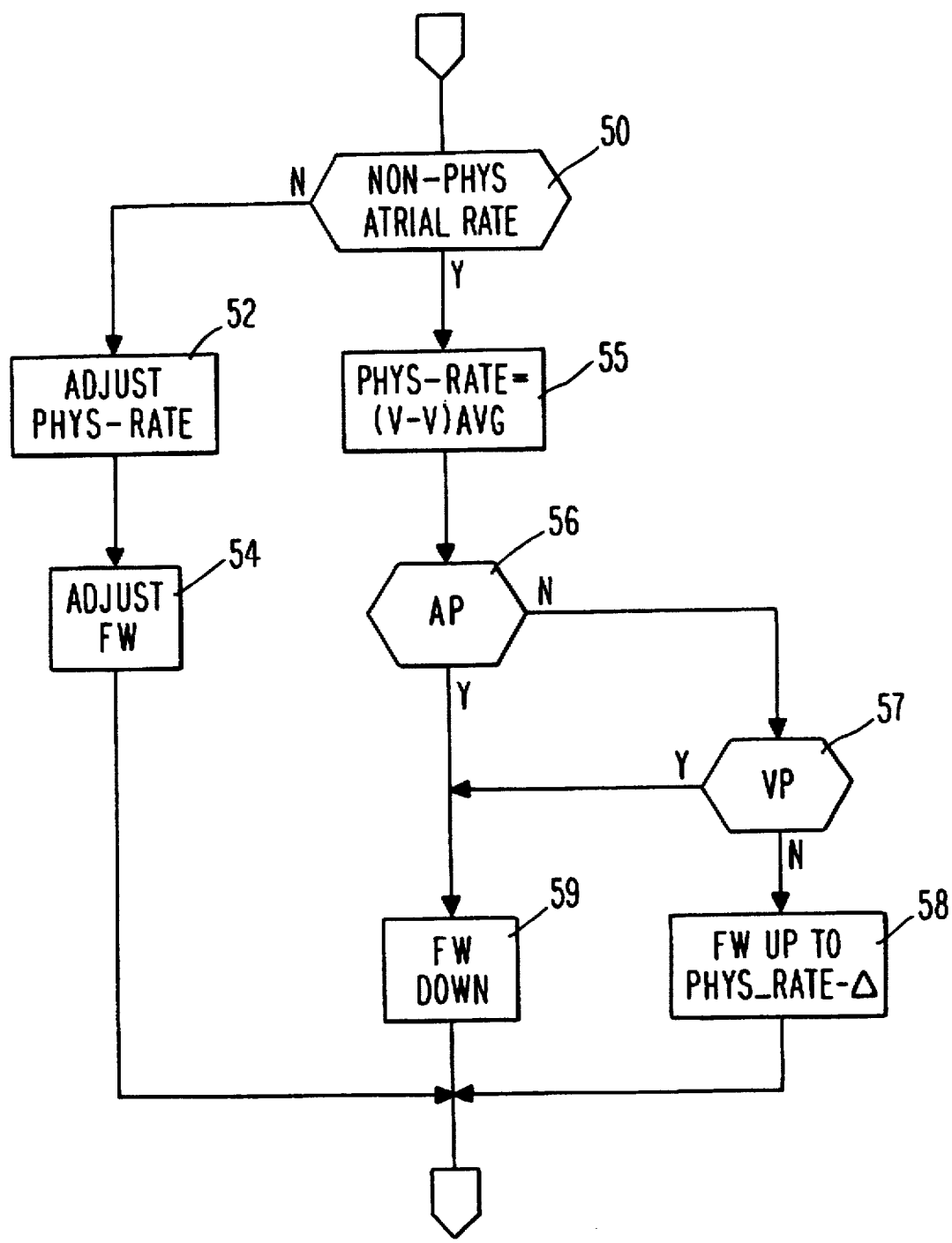
FIG. 5 is a flow diagram showing a routine followed by the pacemaker of this invention for carrying out ventricular rate smoothing when non-physiological atrial signals are sensed at rates above the pacemaker upper rate limit.

Referring now to FIG. 5, there is illustrated a flow diagram of the pacemaker routine for ventricular rate smoothing at the occurrence of a physiologically high atrial rate. At 50, when an atrial event occurs, it is determined whether it is non-physiological. If no, meaning it was physiological, the routine branches to block 52 and adjusts phys_rate appropriately. Then at 54, the flywheel rate is adjusted so that it remains coupled to phys_rate. Returning to 50, if the atrial event has been non-physiological, the routine goes to 55 where it calculates $(V—V)_{avg}$ and sets phys_rate to $(V—V)_{avg}$. At 56 it is determined whether the atrial event was a pace (AP). If yes, the routines goes to 59, and decrements the flywheel (FW) rate. If no, the routine goes to 62 where it is determined whether there has been a V pace. If yes, the routine goes to 59 and adjusts FW down by the predetermined amount. If there has been a VS, the routine goes to block 58 where the flywheel rate is set equal to phys_rate minus Δ, where Δ is nominally 2.5 bpm. It is to be understood that the flywheel rate may be set substantially at the phys_rate, it being preferred to set it incrementally below, as illustrated.

There has been disclosed a system and method for detecting pathological high atrial rates, e.g., atrial fibrillation, and responding by pacing the ventricle in a manner that smooths out large ventricular rate variations without significantly increasing average ventricular heart rate.

I claim:

1. A dual chamber pacing method incorporating smoothing of ventricular rate during episodes of pathologically high atrial heartbeats, comprising:

sensing natural atrial heartbeats and determining when there is an episode of pathological high rate atrial senses, setting a flywheel ventricular pacing rate at about average atrial rate upon a determination of said episode of pathological high rate atrial senses, whenever a ventricular sense occurs during a said episode, adjusting said flywheel pacing rate to substantially track average ventricular rate, and whenever flywheel escape interval times out during a said episode, delivering a ventricular pace and adjusting said flywheel rate incrementally downward.

2. The method as described in claim 1, comprising setting an upper rate limit, and determining when atrial senses are pathological as when they are sensed above said upper rate limit.

3. The method as described in claim 1, comprising continuously determining a phys_rate which substantially reflects the patient's natural atrial rate as long as natural atrial heartbeats are physiological, and setting flywheel rate at a predetermined distance below said $phys_{13}$ rate when said atrial natural atrial heartbeats are physiological.

4. The method as described in claim 3, comprising determining when atrial senses have a rate above a predetermined upper rate limit, and adjusting said flywheel rate to be about the value of said $phys_{13}$ rate when a rate above said upper rate limit is determined.

5. The method as described in claim 4, wherein following a ventricular sense during a said episode, said flywheel rate is adapted to be a predetermined increment below said phys_rate.

6. The method as described in claim 4, wherein when a ventricular pace pulse is delivered during a said episode, the $phys_{13}$ rate and flywheel rate are adjusted down by an increment within the range of 0.25 to 1.0 bpm.

7. A dual chamber pacemaker, said pacemaker having a pulse generator for generating ventricular pace pulses, ventricular sensing means for sensing natural ventricular heartbeat signals, atrial sensing means for sensing natural atrial heartbeat signals, and rate smoothing means for controlling the rate of generating ventricular rate during episodes of pathologically high atrial heart beats, said rate smoothing means comprising:

determining means for determining episodes of pathologically high atrial heartbeats, flywheel pacing rate means for setting the ventricular pacing rate at about the average ventricular heartbeat rate during a said episode, said ventricular pacing rate having a corresponding flywheel escape interval, first flywheel adjusting means for adjusting said flywheel pacing rate upward so as to substantially track average ventricular rate whenever a ventricular sense occurs during a said episode, and second flywheel adjusting means for adjusting said ventricular rate downward whenever said flywheel escape interval times out during a said episode.

8. The pacemaker as described in claim 7, comprising means responsive to a determination of a said episode for determining a measure of atrial rate just before said episode, and third flywheel adjusting means for adjusting ventricular pacing rate at about said average atrial rate upon determination of an episode.

9. The pacemaker as described in claim 7, comprising means for adjusting said ventricular pacing rate to follow a predetermined increment below said average ventricular rate whenever a ventricular sense occurs.

10. A dual chamber pacemaker, said pacemaker having a pulse generator for generating ventricular pace pulses, ventricular sensing means for sensing natural ventricular heartbeat signals, atrial sensing means for sensing natural atrial heartbeat signals and for determining when there is an episode of pathologically high atrial heartbeats, and rate smoothing means for controlling ventricular rate during episodes of pathologically high atrial heart beats, said rate smoothing means comprising:

control means for controlling the escape interval of said ventricular pace generator, said escape interval corresponding to a flywheel rate, means for cyclically determining the average ventricular rate during a said episode, and flywheel means for cyclically adjusting said flywheel rate after ventricular sense and ventricular pace events to substantially track said average ventricular rate during said episode.

11. The pacemaker as described in claim 10, wherein said flywheel means has means operative after a ventricular sense for adjusting the flywheel escape interval to correspond to a flywheel rate which is a predetermined increment below said average ventricular rate.

12. The pacemaker as described in claim 10, comprising means for adjusting said flywheel rate upward by a first predetermined increment whenever there is a ventricular sense during a said episode.

13. The pacemaker as described in claim 12, wherein said flywheel means further comprises means for adjusting said flywheel rate downward by a second predetermined increment whenever the flywheel escape interval times out and a ventricular pace pulse is delivered.

* * * * *

UNITED STATES PATENT AND TRADEMARK OFFICE
CERTIFICATE OF CORRECTION

PATENT NO. : 5,792,193
DATED : August 11, 1998
INVENTOR(S) : Gustaaf A.P. Stoop

It is certified that error appears in the above-indentified patent and that said Letters Patent is hereby corrected as shown below:

Col. 3, line 27, "$phys_{13}$" should read --phys_rate--

Col. 3, line 46, "$phys_{13}$" should read --phys_rate--

Col. 3, line 49, "$phys_{13}$" should read --phys_rate--

Col. 5, line 40 (claim 3), "$phys_{13}$ rate" should read --phys_rate--

Col. 5, line 45 (claim 4), "$phys_{13}$ rate" should read --phys_rate--

Col. 5, line 53 (claim 6), "$phys_{13}$ rate" should read --phys_rate--

Signed and Sealed this

Twenty-fourth Day of November, 1998

Attest:

BRUCE LEHMAN

*Attesting Officer*     *Commissioner of Patents and Trademarks*